(12) United States Patent
Maison et al.

(10) Patent No.: US 8,785,641 B2
(45) Date of Patent: Jul. 22, 2014

(54) SYNTHESIS OF TRIPODAL CATECHOL DERIVATIVES HAVING AN ADAMANTYL BASIC FRAMEWORK FOR FUNCTIONALIZING SURFACES

(75) Inventors: Wolfgang Maison, Winsen (DE); Faiza Khalil, Mucke (DE); Elisa Franzmann, Wettenberg-Wißmar (DE)

(73) Assignee: Justus-Liebig-Universitat Giessen, Giessen (DE)

( * ) Notice: Subject to any disclaimer, the term of this patent is extended or adjusted under 35 U.S.C. 154(b) by 0 days.

(21) Appl. No.: 13/821,319

(22) PCT Filed: Sep. 7, 2011

(86) PCT No.: PCT/EP2011/065480
§ 371 (c)(1),
(2), (4) Date: Jun. 3, 2013

(87) PCT Pub. No.: WO2012/032084
PCT Pub. Date: Mar. 15, 2012

(65) Prior Publication Data
US 2013/0245269 A1 Sep. 19, 2013

(30) Foreign Application Priority Data
Sep. 10, 2010 (EP) .................................. 10176286

(51) Int. Cl.
C07C 233/22 (2006.01)
C07C 231/02 (2006.01)
C07D 217/06 (2006.01)
C07D 493/10 (2006.01)

(52) U.S. Cl.
USPC ............ 546/140; 546/146; 564/153; 568/718

(58) Field of Classification Search
None
See application file for complete search history.

(56) References Cited

U.S. PATENT DOCUMENTS

| 7,456,323 B2 * | 11/2008 | Yoshitomo et al. ........... 568/436 |
| 2006/0063834 A1 | 3/2006 | Frangioni et al. |
| 2008/0169059 A1 | 7/2008 | Messersmith et al. |

FOREIGN PATENT DOCUMENTS

WO  WO-2009/111611  9/2009

OTHER PUBLICATIONS

W. Maison, et al., "Synthesis of Rigid Multivalent Scaffolds Based on Adamantane", *Organic Letters*, 6(24):4567-69 (2004).
A. Oganesyan, et al., "High Yield Selective Acylation of Polyamines: Proton as Protecting Group", *Organic Letters*, 9(24):4967-70 (2007).
K. Nasr, et al., "Rigid Multivalent Scaffolds Based on Adamantane", *J. Org. Chem.*, 73(3):1056-60 (2008).
N. Pannier, et al., "Rigid C3-Symmetric Scaffolds Based on Adamantane", *Eur. J. Org. Chem*.:1278-84 (2008).
International Search Report in International Application No. PCT/EP2011/065480 issued/mailed by the European Patent Office on Dec. 22, 2011 (6 pages).

* cited by examiner

*Primary Examiner* — Zinna Northington Davis
(74) *Attorney, Agent, or Firm* — Marshall, Gerstein & Borun LLP

(57) ABSTRACT

The present invention describes tripodal catechol derivatives with an adamantyl basic framework for the functionalization of surfaces, methods for their production and use. The remaining fourth bridgehead position is easily suitable to be further functionalised via so-called click reactions, by way of example with biomolecules, dyes, radiomarkers, polyethylene glycol or active agents.
The compounds according to the present invention have the general formula $X\text{-}Ad[(CH_2)_n\text{-}YZ]_3$, wherein A stands for the adamantyl skeleton, X stands for a group $-(CH_2)_p-R^5$, wherein p=0 to 10 and $R^5$ is selected from $-H$, $-NH_2$, $-NO_2$, $-OH$, $-SH$, $-O-NH_2$, $-NH-NH_2$, $-N=C=S-$, $-N=C=O-$, $-CH=CH_2$, $-C\equiv CH$, $-COOH$, $-(C=O)H$, $-(C=O)R^6$ Y stands for $-CH_2-$, $-CH=CH-$, $-C\equiv C-$, $-O-$, $-S-$, $-S-S-$, $-NH-$, $-O-NH-$, $-NH-O-$, $-HC=N-O-$, $-O-N=CH-$, $-NR^1-$, -aryl-, -heteroaryl-, $-(C=O)-$, $-O-(C=O)-$, $-(C=O)-O-$, $-NH-(C=O)-$, $-(C=O)-NH-$, $-NR^1-(C=O)-$, $-(C=O)-NR^1-$, $-NH-(C=O)-NH-$, $-NH-(C=S)-NH-$, $R^1$ stands for an alkyl group, $R^6$ for an alkyl, alkenyl, alkynyl, aryl or heteroaryl group, and Z stands for a catechol derivative.
The production of the compounds occurs by reacting a compound $X\text{-}Ad[(CH_2)_n\text{-}Y']_3$ with a reagent Y"Z to the corresponding compound $X\text{-}Ad[(CH_2)_n\text{-}YZ]_3$ and subsequently purifying the reaction product.
Y' and Y" are hereby precursors of Y. The compounds according to formula (I) according to the present invention are suitable to be used in a method to functionalize surfaces. The X group of the compounds according to the present invention is suitable to be optionally coupled to an effector, for example, by means of click chemistry.

12 Claims, No Drawings

SYNTHESIS OF TRIPODAL CATECHOL DERIVATIVES HAVING AN ADAMANTYL BASIC FRAMEWORK FOR FUNCTIONALIZING SURFACES

CONTINUING DATA

This application is a 371 application of PCT/EP2011/065480 filed Sep. 7, 2011.

BACKGROUND OF THE INVENTION

1. Field of the Invention

The present invention relates to the fields of organic chemistry and material sciences.

2. Brief Description of Related Technology

The state of the art recognizes numerous methods for the functionalisation of surfaces. Such functionalisations are used in order to modify the material properties of the surfaces in a targeted manner. Such functionalisations should be as durable as possible and allow for a highly defined loading of the surface.

In the field of medical technology, special importance is placed on functionalised surfaces. Implants should—by way of example in the dental industry and orthopedics (joint replacement)—be as biocompatible as possible, i.e. by not, inter alia, having a tendency towards biofouling, not causing any inflammatory reactions and not being seeded with pathogenic microorganisms. Furthermore, they must permanently resist heavy mechanical strain.

Medical implants frequently comprise the metals iron and/or titanium, while dental implants also contain apatite. Until now, monomeric derivatives of the catecholamine have been used as a surface binder to which different functional molecules such as antibiotics or PEG were subsequently bonded. With such conjugates, it was possible to detect an increased resistance of the surfaces against biofouling. Polymer structures which imitate mussel adhesion proteins are an alternative to monomeric catechol derivatives. These are used as a biomimetic adhesive.

With the help of monomeric catechol derivatives, metal surfaces are suitable to be easily functionalised; however, this functionalization unfortunately comes with low durability. This is particularly disadvantageous in the case of heavy material stress such as applications in the dental industry. Although polymer structures allow for an extremely strong connection, they do not allow for a targeted or defined functionalisation of the surface as is desired, by way of example, for implants.

Adamantane is a rigid molecule which comprises three condensed six-member carbocyclic rings. The carbon atoms 1, 3, 5 and 7 of the adamantane are bridgehead atoms. Adamantane derivatives are known and used in medicine and material sciences. When these adamantane derivatives carry identical substituents at three bridgehead positions, they comprise a tripodal arrangement.

US 2006/0063834 A1 describes different adamantane derivatives with tripodal arrangement, methods for their production and their use for pharmaceutical compositions. However, no adamantane derivatives are disclosed which are suitable to functionalise surfaces.

In A Oganesyan, I A Cruz, R B Amador, N A Sorto, J Lozano, C E Godinez, J Anguiano, H Pace, G Sabih, C G Gutierrez: "High Yield Selective Acylation of Polyamines: Proton as Protecting Group", Org Lett 2007, 9, 4967-4970 describes the selective acylation of polyamines which comprise several identical or similar amine functions. The authors of the paper state that the omnipresence of polyamide bindings in biological molecules converts the selective acylation into an interesting approach for the production of biomimetic molecules. However, no compounds are disclosed comprising substituted 3,4-dihydroxybenzyl groups as ligands of the adamantane which serve to functionalise surfaces.

Methods for the production of rigid tripodal compounds based on adamantane are described in W Maison, J V Frangioni, N Pannier: "Synthesis of Rigid Multivalent Scaffolds Based on Adamantane", Org Lett 2004, 6, 4567-4569 and in N Pannier, W Maison: "Rigid $C_3$-Symmetric Scaffolds Based on Adamantane", Eur J Org Chem 2008, 1278-1284 and in K Nasr, N Pannier, J V Frangioni, W Maison: "Rigid Multivalent Scaffolds Based on Adamantane", J Org Chem 2008, 73, 1058-1060. The production of trivalent adamantane skeletons with ligands comprising catechol units is not disclosed there.

Functionalisations of surfaces with the monomeric derivatives of the catecholamine known up to now comprise the disadvantage that these functionalisations are not sufficiently permanent.

SUMMARY OF THE INVENTION

The invention at hand overcomes the disadvantages of the state of the art by providing trivalent adamantane skeletons with ligands comprising catechol units. The design of the compounds hereby occurs biometrically and is oriented towards mussel adhesion proteins and siderophores, which naturally cause high affinity bindings to surfaces. The compounds according to the present invention comprise tripodal skeletons on the basis of the adamantane to which three catechol units are bound in the bridgehead positions. The remaining fourth bridgehead position is easily suitable to be further functionalised via so-called click reactions, e.g. with biomolecules, dyes, radiomarkers, polyethylene glycol or active agents.

DETAILED DESCRIPTION

The aim of the present invention is to provide compounds which allow for a durable functionalisation and a highly defined loading of surfaces, and methods for the production of these compounds.

The present invention describes tripodal catechol derivatives with an adamantyl basic framework for the functionalisation of surfaces, and methods for their production and use. The design of the compounds hereby occurs biometrically and is oriented towards mussel adhesion proteins, which naturally cause high affinity bindings to surfaces. A fourth remaining position of the adamantane skeleton is suitable to be optionally functionalised by so-called click reactions, for example with biomolecules, polyethylene glycol or active agents.

The task, namely to provide compounds which allow for a durable functionalisation and a highly defined loading of surfaces is achieved according to the present invention via compounds according to formula (I):

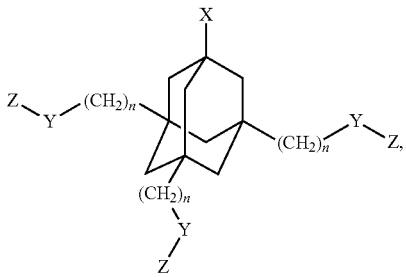

wherein
n is an integer between 0 and 10,
Y is selected from —CH$_2$—, —CH=CH—, —C≡C—, —O—, —S—, —S—S—, —NH—, —O—NH—, —NH—O—, —HC=N—O—, —O—N=CH—, —NR$^1$—, -aryl-, -heteroaryl-, —(C=O)—, —O—(C=O)—, —(C=O)—O—, —NH—(C=O)—, —(C=O)—NH—, —NR$^1$—(C=O)—, —(C=O)—NR$^1$—, —NH—(C=O)—NH—, —NH—(C=S)—NH—, wherein R$^1$ stands for a linear alkyl group with 1 to 10 C atoms or a branched or cyclic alkyl group with 3 to 10 C atoms,
Z is selected from

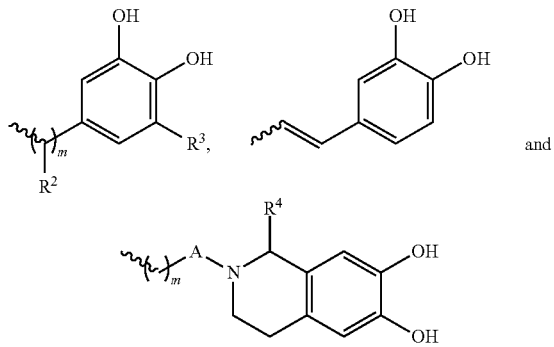

and with
m=an integer between 0 and 10,
R$^2$=—H, —OH or —COOH,
R$^3$=—H, —OH
A=no atom or —(C=O)—
R$^4$=—H or

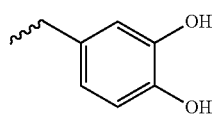

and
X stands for a group —(CH$_2$)$_p$—R$^5$, wherein p=0 to 10 and R$^5$ is selected from —H, —NH$_2$, —NO$_2$, —OH, —SH, —O—NH$_2$, —NH—NH$_2$, —N=C=S—, —N=C=O—, —CH=CH$_2$, —C≡CH, —COOH, —(C=O)H, —(C=O)R$^6$, wherein the hydroxy, thio, amino or C=O groups are optionally suitable to be protected by a protective group, —N$_3$, —OR$^6$, —COOR$^6$, —NHR$^6$, —NR$^6$R$^7$, —CO—NHR$^6$, —CONR$^6$R$^7$, —NH—CO—R$^6$, 4-(2,5-dioxopyrrol-1-yl), wherein R$^6$ and R$^7$ stand independently of one another for a linear alkyl group with 1 to 10 C atoms, a linear alkenyl or alkynyl group with 2 to 10 C atoms, a branched alkyl, alkenyl or alkynyl group with 3 to 10 C atoms or a cyclic alkyl or alkenyl group with 3 to 10 C atoms, or
X stands for a branched alkyl, alkenyl or alkynyl group with 3 to 10 C atoms or a cyclic alkyl, alkenyl oder alkynyl group with 3 to 10 C atoms or for an aryl or heteroaryl group, wherein, in the event that X is a branched alkyl, alkenyl and alkynyl group, a cyclic alkyl or alkenyl group, an aryl or heteroaryl group, one C atom of this group X is optionally suitable to carry one group R$^5$ according to the definition above.

The compounds according to the present invention, the method for their production and the use of these compounds are explained hereinafter.

The invention is not limited to one of the embodiments described hereinafter; rather, it is suitable to be modified in various different ways.

All of the characteristics and advantages originating from the claims, description and figures (including constructive details, spatial arrangements and processing steps) are suitable to be essential to the invention, both in themselves and in the most various combinations.

The compounds according to formula (I) according to the present invention allow for a durable functionalisation and a highly defined loading of surfaces. Surfaces which are suitable to be functionalised and loaded comprise metals, metal oxides, apatite, glass and mixtures thereof. The term "apatite" hereby comprises both compounds following the general formula Ca$_5$(PO$_4$)$_3$(F,Cl,OH), in which the concentration of fluoride, chloride and hydroxyl ions is freely exchangeable, and the single minerals fluoroapatite, chloroapatite and hydroxylapatite.

"Highly defined loading" is understood to mean that the loading of the surface allows for a gap-free coating of the material in the form of a monolayer. "Monolayer" is understood to mean a layer of molecules according to the present invention on the surface which has a height of just a single molecule. A "functionalisation" is the addition of functional groups to the surface of a material via chemical synthesis methods. A coating of surfaces with the compounds according to the present invention thus represents a functionalisation of these surfaces. An effector molecule is optionally suitable to be bonded to the group X. This represents another functionalisation. An effector is a molecule or a molecule component which causes a physical, chemical, biochemical or biological process or controls, activates or inactivates such an effect. Examples for effectors are dyes, radioactive molecules, biomolecules such as amino acids, sugars, peptides, proteins, DNA, RNA, polymers such as ethylene glycol and derivatives thereof, and active agents. Substances are referred to as active agents if they cause a specific effect or a reaction in low doses within an organism.

Due to the multivalent binding of the compounds according to formula (I), this functionalisation is durable in comparison to molecular exchange processes on the surface (such as the hydrolysis of the coupling in aqueous media) and also in comparison to mechanical strain.

In the context of the present invention, alkyl groups with 1 to 10 carbon atoms are selected from methyl, ethyl, n-propyl, isopropyl, 1-butyl, 2-butyl, tert-butyl, 1-pentyl, 2-pentyl, 3-pentyl, 3-methylbutyl, 2,2-dimethylpropyl, and all the isomers of hexyl, heptyl, octyl, nonyl and decyl. Alkenyl and alkynyl groups comprise at least two carbon atoms. They are selected from ethenyl and ethinyl groups and all isomers of propenyl, butenyl, pentenyl, hexenyl, heptenyl, octenyl, nonenyl, decenyl, ethinyl, propinyl, butinyl, pentinyl, hexinyl, heptinyl, octinyl, noninyl and decinyl groups. Branched alkyl, alkenyl and alkynyl groups comprise at least three carbon atoms and are selected according to the present invention from the aforementioned homologs with this minimum number of carbon atoms.

It is known to persons skilled in the art that cyclic alkyl and alkenyl groups have to comprise at least three carbon atoms. In the context of the present invention, "annular" groups are understood to mean such groups in which all carbon atoms are involved in the ring formation. Furthermore, "cyclic" groups are suitable to also comprise acyclic carbon atoms. In the context of the present invention, annular alkyl and alkenyl groups are propyl, butyl, pentyl, hexyl, heptyl, octyl, nonyl, decyl, propenyl, butenyl, pentenyl, hexenyl, heptenyl, octenyl, nonenyl and decenyl rings. If the groups X, $R^6$ and/or $R^7$ are cyclic alkyl or alkenyl groups, they are selected from the aforementioned annular alkyl and alkenyl groups which do not carry further substituents, and from the aforementioned annular alkyl and alkenyl groups which are themselves bonded to one or several acyclic alkyl, alkenyl or alkynyl groups. In the latter case, the binding of the cyclic alkyl or alkenyl group to the C1 atom of the adamantane skeleton (provided that the cyclic group represents X) or to the respective atom of the group $R^5$ (provided that the cyclic group represents $R^6$ or $R^7$) is suitable to occur via a cyclic or acyclic carbon atom of the cyclic alkyl or alkylene group. According to the above definition of the term "alkyl group", cyclic alkyl groups also comprise a total of 10 carbon atoms maximum.

According to the present invention, the group X is a group —$(CH_2)_p$—$R^5$. If $R^5$ is —$NH_2$, —OH, —SH, —O—$NH_2$, —NH—NH—COOH, —(C=O)H, —(C=O)$R^6$, these groups are optionally suitable to be protected by a protective group. Protective groups for hydroxy, thiol, amino, carbonyl and carboxyl groups are known by persons skilled in the art. They are able to use these protective groups, i.e. to introduce and, if required, cleave them off again, without leaving the scope of protection of the patent claims.

By way of non-exhaustive example, the following protective groups are to be named:
- for the OH group: methoxy methyl ether (MOM), β-methoxy ethoxy methyl ether (MEM), silyl ether, 2-tetrahydropyranyl (THP), Acetyl (Ac), benzoyl (Bz), benzyl (Bn, Bnl), dimethoxytrityl (DMT), methoxytrityl (MMT), p-methoxy benzyl ether (PMB), methylthiomethyl ether, pivaloyl (piv), methylether, ethoxyethyl ether (EE)
- for the SH group: tert-butyl, 2-tetrahydropyranyl, acetyl, 2-nitropyranyl, phenacyl, (cumarin-4-yl)methyl
- for the $NH_2$ group: 1-(1-adamantyl)-1-methoxycarbonyl (ADPOC), allyl-oxycarbonyl (ALLOC), benzyloxycarbonyl (abbreviated by Z or Cbz), 9-fluorenylmethoxycarbonyl (FMOC), p-methoxybenzyl carbonyl (Moz, MeOZ), tert-butyloxycarbonyl (BOC), acetyl (ac), benzoyl (Bz), benzyl (Bn, Bnl), p-methoxybenzyl (PMB), 3,4-dimethoxybenzyl (DMPM), p-methoxyphenyl (PMP), Tosyl (ts), sulfonamides
- for the carbonyl group (in aldehydes and ketones): the reaction with diols to acetals or ketals
- for the COOH group: methylester, benzyl ester, tert-butyl ester, silyl ester, orthoester, oxazolines According to the present invention, aryl groups are understood to mean phenyl, naphthyl and anthracenyl groups.

Heteroaryl groups are selected from furanyl, pyrrolyl, thiophenyl, imidazolyl, pyrazolyl, triazolyl, thiazolyl, oxazolyl, isooxazolyl, one oxadiazolyl, pyridinyl, pyrazinyl, pyrimidinyl, pyridazinyl, one triazinyl, one tetrazinyl, 1,4-dioxinyl, one thiazinyl, one oxazinyl, one azepinyl, a diazepinyl, benzofuranyl, isobenzofuranyl, indolyl, isoindolyl, benzothiophenyl, benzo[c]thiophenyl, benzimidazolyl, purinyl, indazolyl, benzoxazolyl, benzisoxazolyl, benzothiazolyl, quinolinyl, isochinolinyl, chinoxalinyl, acridinyl, chinazolinyl and cinnolinyl.

If Y stands for "-aryl-" or "heteroaryl-", two carbon atoms of this aryl or heteroaryl group are connected with the alkylene groups —$(CH_2)_n$ or —$(CH_2)_m$ according to formula (I) and the definition of Z.

In an advantageous embodiment, Y is selected from no atom, —$CH_2$—, —NH—(C=O)—(C=O)—NH—, —$NR^1$—, wherein $R^1$ is as defined above.

In another advantageous embodiment, n is an integer between 0 and 3.

In another advantageous embodiment, m is an integer between 0 and 3.

Particularly advantageously, n and m stand independently of one another for integers between 0 and 3.

In a further advantageous embodiment, Z is a group

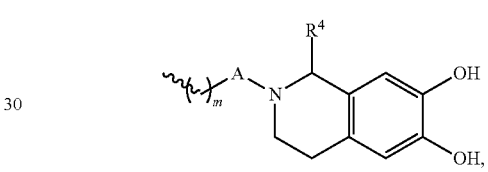

wherein m, A and $R^4$ are defined as above. Advantageously, m is hereby an integer between 0 and 3.

In a particularly advantageous embodiment, the group YZ is selected from

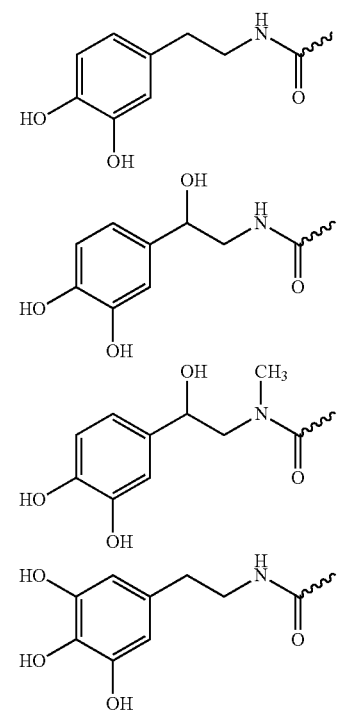

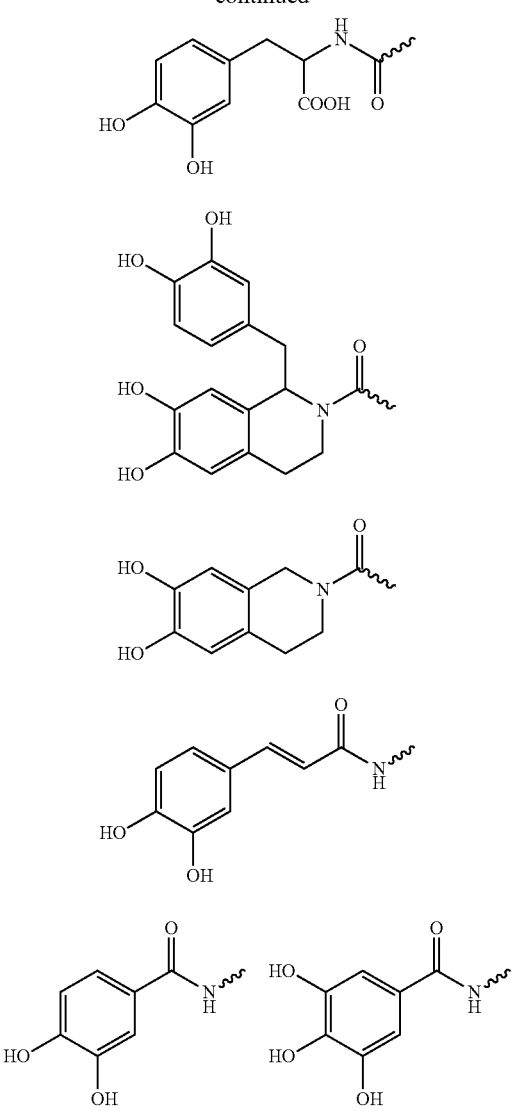

These particularly advantageous YZ groups are derived from the following catechol derivatives:

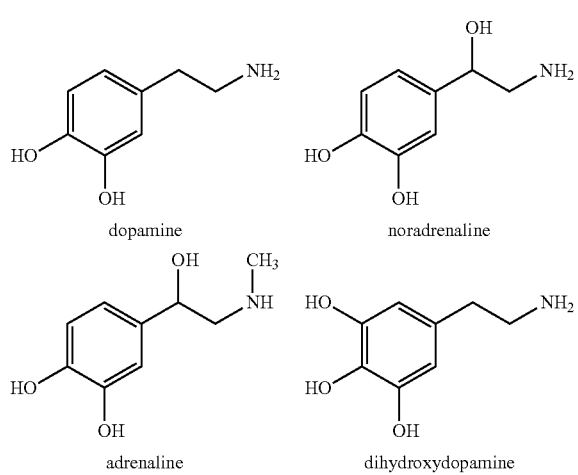

dihydroxyphenylalanine dihydroxytetrahydroisoquinoline 1-(3,4-dihydroxybenzyl)-1,2,3,4-tetrahydroisoquinoline-6,7-diol 3,4-dihydroxy-benzoic acid gallic acid 3,4-dihydroxycinnamic aicd In the context of the present invention, the compounds dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline and 3,4-dihydroxybenzoic acid are referred to as "catechol derivatives".

In a further advantageous embodiment, X represents a group $(-CH_2)_p-R^5$, wherein p represents an integer between 0 and 3 and $R^5$ is defined as in claim 1.

In a further advantageous embodiment, X stands for $-(CH_2)_p-R^5$, wherein $R^5$ is selected from —H, —OH, —$NH_2$, —$NO_2$, —NH—$NH_2$, —$NHR^6$, —$NR^6R^7$, —O—$NH_2$, —NH—(C=O)—C≡CH, —C≡CH, —N=C=S, —N=C=O, —COOH, —(C=O)H, —(C=O)$R^6$ and wherein p represents an integer between 0 and 3, and $R^6$ and $R^7$ are as defined above.

The compounds according to the present invention according to formula (I) are produced by reacting a compound X-Ad[$(CH_2)_n$—Y']$_3$ with a reagent Y"Z to the corresponding compound X-Ad[$(CH_2)_n$—YZ]$_3$ and by subsequent purification of the reaction product, wherein Ad stands for the adamantyl skeleton and Y' for a precursor of the group Y according to formula (I) and wherein X, Z and n are defined as in formula (I).

Precursor is hereby understood to refer to a functional group which is converted via reaction with another functional group acting as precursor or a further reagent acting as precursor into a functional group according to formula (I).

Compounds of the formula X-Ad[(CH$_2$)$_p$—Y']$_3$ are known. Persons skilled in the art are able to commercially purchase them or produce them independently with the help of their specialist knowledge following known synthesis procedures.

In an advantageous embodiment, X is a hydrogen atom.

In another advantageous embodiment, X is a group —(CH$_2$)$_p$—R$^5$, wherein p represents an integer between 0 and 3, and R$^5$ is selected from —OH, —NH$_2$, —NO$_2$, —NH—NH$_2$, —NHR$^6$, —NR$^6$R$^7$, —O—NH$_2$, —NH—(C=O)—C≡CH, —C≡CH, —N=C=S, —N=C=O, —COOH, —(C=O)H, —(C=O)R$^6$, wherein R$^6$ and R$^7$ are defined as in formula (I). As already indicated, these groups may be optionally protected via a protective group (Pg). If these groups are protected, this occurs before the reaction with the reagent Y"Z, so that in this case Pg-X-Ad[(CH$_2$)$_n$—Y']$_3$ is reacted with the reagent Y"Z to the corresponding compound Pg-X-Ad[(CH$_2$)$_n$—YZ]$_3$.

Suitable protective groups are described above. It is known to persons skilled in the art how to introduce these protective groups and remove them again. Persons skilled in the art are able to apply this knowledge without leaving the scope of protection of the patent claims.

The purification of the reaction product occurs, by way of example, by removing the solvent, adding the residue to a mixture comprising a polar aprotic solvent such as ethyl acetate and a diluted mineral acid, e.g. diluted hydrochloric acid, washing with a saturated KHSO$_4$ solution and drying.

In an advantageous embodiment, Y"Z is a catecholamine selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. In this case, X-Ad[(CH$_2$)$_n$—Y']$_3$ or Pg-X-Ad[(CH$_2$)$_n$—YZ]$_3$ is reacted with the catecholamine in the presence of an activating reagent and a coupling additive. Y' is hereby a carboxylic acid residue or a derivative thereof. Suitable activating reagents are, by way of example, EDC, DCC, DCI, PyClop, HBTU, HATU, HOSu, TBTU, T3P, BopCl and 3-Cl-1-pyridinium iodide. The substances HOBT, HOAt, HONB and NHS known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

If the catecholamine Y"Z is adrenaline or noradrenaline, their aliphatic hydroxy group is optionally protected from the coupling with a protective group. The carboxyl group of the dihydroxyphenylalanine is equally suitable to be protected from the coupling if it represents Y"Z.

If a protective group Pg has been introduced and/or protected adrenaline, noradrenaline or dihydroxyphenylalanine has been used, these protective groups are removed at the end, and the deprotected product is subsequently purified.

In another advantageous embodiment, Y"Z is 3,4-dihydroxybenzoic acid or a similar derivative such as 3,4-dihydroxycinnamic acid or gallic acid. In this case, X-Ad[(CH$_2$)$_n$—Y']$_3$ or Pg-X-Ad[(CH$_2$)$_n$—Y']$_3$ is reacted with 3,4-dihydroxybenzoic acid, 3,4-dihydroxycinnamic acid or gallic acid in the presence of an activating reagent and a coupling additive. Y' is hereby advantageously an alcohol or amine function. Suitable activating reagents are, by way of example, EDC, DCC, DCI, PyClop, HBTU, HATU, HOSu, TBTU, T3P, BopCl and 3-Cl-1-pyridinium iodide. The substances HOBT, HOAt, HONB and NHS known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X-Ad[(CH$_2$)$_n$—Y']$_3$ or Pg-X-Ad[(CH$_2$)$_n$—Y']$_3$ are reacted with the catecholamine in the presence of a means of reduction. Y' is hereby an aldehyde or a ketone. Suitable means of reduction are, by way of example, NaBH$_4$, NaBH$_3$CN, NaBH(OAc)$_3$, as well as H$_2$ and metal catalysts. Persons skilled in the art know different solvents to be used in the methods mentioned. They are able to independently produce these combinations of means of reduction and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X-Ad[(CH$_2$)$_n$—Y']$_3$ oder Pg-X-Ad[(CH$_2$)$_n$—Y']$_3$ with a suitable leaving group Y' are reacted with the catecholamine. Suitable leaving groups are, by way of example, —OTs, OMs, —OTf and halides. Persons skilled in the art know different solvents to be used in the methods mentioned.

They are able to independently produce these combinations of leaving groups and solvents using their conventional knowledge and standard literature.

In another advantageous embodiment, Y"Z is a catecholamine, selected from dopamine, noradrenaline, adrenaline, dihydroxydopamine, dihydroxyphenylalanine, 1-(3,4-dihydroxybenzyl)-1,2,3,4-tetrahydroisoquinoline-6,7-diol and dihydroxytetraisoquinoline. X-Ad[(CH$_2$)n—Y']$_3$ or Pg-X-Ad[(CH$_2$)n—Y']$_3$ is reacted with the catecholamine. Y' is hereby an isothiocyanate or an isocyanate. Persons skilled in the art know different solvents to be used in the methods mentioned. They are able to independently produce these combinations of means of reduction and solvents using their conventional knowledge and standard literature.

In a further advantageous embodiment, Y"Z is 3,4-dihydroxybenzaldehyde. X-Ad[(CH$_2$)$_n$—Y']$_3$ or Pg-X-Ad[(CH$_2$)$_n$—Y']$_3$ is reacted with 3,4-dihydroxybenzaldehyde. Y' is hereby an O-alkylhydroxylamine or the corresponding hydrohalide. Persons skilled in the art know different solvents to be used in the methods mentioned. They are able to independently produce these combinations of means of reduction and solvents using their conventional knowledge and standard literature.

In another advantageous embodiment, Y"Z is 3,4-dihydroxybenzoic acid or a similar derivative such as 3,4-dihydroxycinnamic acid or gallic acid. X-Ad[(CH$_2$)$_n$—Y']$_3$ or Pg-X-Ad[(CH$_2$)$_n$—Y']$_3$ is reacted with 3,4-dihydroxybenzoic acid or a similar derivative such as 3,4-dihydroxycinnamic acid or gallic acid in the presence of an activating reagent such as DCC or EDC or with catalytic amounts of an acid such as HCl, H$_2$SO$_4$ or p-toluenesulfonic acid. Y' is hereby advantageously an alcohol function. Persons skilled in the art know different solvents to be used in the methods mentioned. They are able to independently produce these combinations of activating reagents, coupling additives, bases and solvents using their conventional knowledge and standard literature.

The compounds according to formula (I) according to the present invention are suitable to be used in a method to functionalise surfaces. The functionalisation hereby occurs via dip and rinse by dipping the surfaces to be functionalised into a solution of the compounds according to the present invention.

The compounds according to the present invention are advantageously dissolved in an aqueous buffer solution which comprises a salt concentration significantly higher than physiological salt concentrations (0.9 wt.-% of NaCl). MOPS (3(N-morpholine)-propane sulfonic acid) is, by way of example, a suitable buffer. NaCl and $K_2SO_4$ and mixtures thereof are suitable salts. The salt concentration advantageously amounts to between 10 and 20 wt.-% and the buffer concentration to between 0.05 and 0.2 mmol.

The X group of the compounds according to the present invention is suitable to be optionally coupled to an effector. The coupling of X to the effector is hereby suitable to be carried out both in solution, i.e. before the functionalisation of the surface, as well as on the surface, i.e. after the functionalisation of the surface. Effectors are, by way of example, ether groups, ester groups, heteroaromatic compounds, dyes, metal complexes, polymers (for example polyethylene glycols), pharmaceutical active agents (for example antibiotics, bisphosphonates), biomolecules (for example an amino acid), peptides, carbohydrates and terpenes. If the effector is a polymer and if this is a polyethylene glycol, it is advantageously a grouping —$(O-CH_2-CH_2)_q-R^5$ or —$(CH_2-CH_2-O)_q-R^5$, wherein q is a number between 1 and 10 and $R^5$ is defined as described under formula 1.

In an advantageous embodiment, the coupling of X is carried out by means of click chemistry. "Click reactions" are understood by persons skilled in the art to be energetically favoured reactions which run specifically and result in a single product. These are efficient reactions which are suitable to be carried out very easily. Click reactions are used in molecular biology, the development of active agents, biotechnology, macromolecular chemistry and material sciences. The concept of the click reaction was established by K. Barry Sharpless and describes reactions which
- are structured in a modular manner,
- comprise a wide scope of application,
- are suitable to be carried out with high yields,
- occur stereospecifically,
- allow for simple reaction conditions (as non-sensitive as possible against water and oxygen),
- occur in environmentally-friendly solvents and/or solvents which are easily removable, such as water, or occur in a solvent-free manner,
- require simple purification (extraction, phase separation, distillation or crystalisation) or no purification at all.

"Click reactions" are, in general, strongly thermodynamically favoured. This is frequently more than 84 kJ/mol, which results in a fast reaction with high selectivity for a single product. These are frequently carbon-heteroatom bond formations.

Chemical reactions which fulfill these criteria are:
- the carbonyl chemistry of the "non-aldol type", such as the formation of urea, thiourea, oximes, imines, aromatic heterocycles and hydrazones, and the formation of carbamides and amides,
- cyclo additions to unsaturated C—C bonds, in particular 1,3-dipolar cyclo additions such as the Huisgen cycloaddition, and also Diels-Alder reactions,
- nucleophilic substitutions, in particular the ring opening of strained, electrophilic heterocycles such as aziridines and epoxides,
- addition reactions at C—C multiple bonds, mostly in an oxidative manner, such as epoxidation, aziridination or dihydroxylation, but also Michael additions of Nu-H, wherein Nu is a nucleophile.

In another advantageous embodiment, the coupling of the effector to the X group occurs via conventional substitution or addition reactions which do not belong to the abovementioned conditions of a click reaction. These conventional reactions comprise, by way of example, the formation of ether, the esterification of a carboxylic acid or the formation of amide.

Particularly advantageously, the surfaces to be functionalised are metallic surfaces comprising iron and/or titanium or surfaces comprising apatite. It is known to persons skilled in the art that bones of vertebrates comprise approximately 50% apatite, approximately 70% dentine and more than 95% tooth enamel. Modern dental prostheses, such as dental fillings and implants, frequently comprise apatite and/or devices which comprise iron and/or titanium. It is furthermore known that the surfaces of endosprostheses, for example for hip and knee joints, comprise iron and/or titanium. The compounds according to the present invention according to formula (I) as well as the compounds which are suitable to be obtained from them and coupled to an effector, are therefore suitable for the surface functionalisation of dental and joint endosprotheses.

PRACTICAL EMBODIMENTS

Synthesis plan for practical embodiments 1 to 3

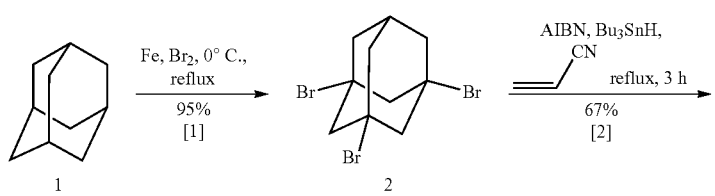
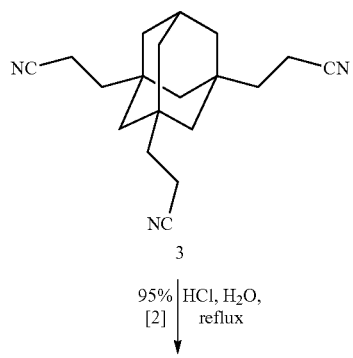

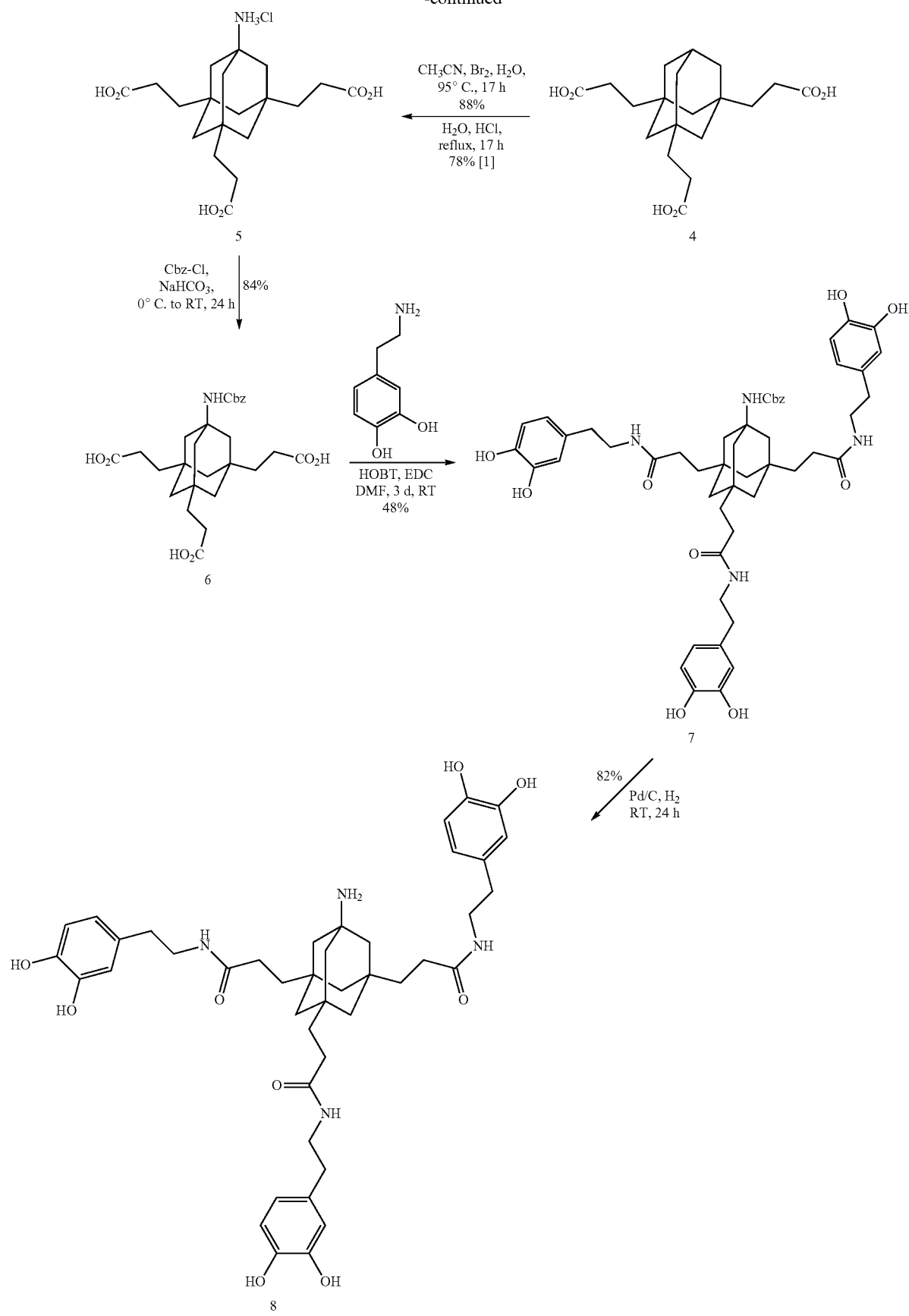

Synthesis plan 2 for practical embodiments 4 to 7
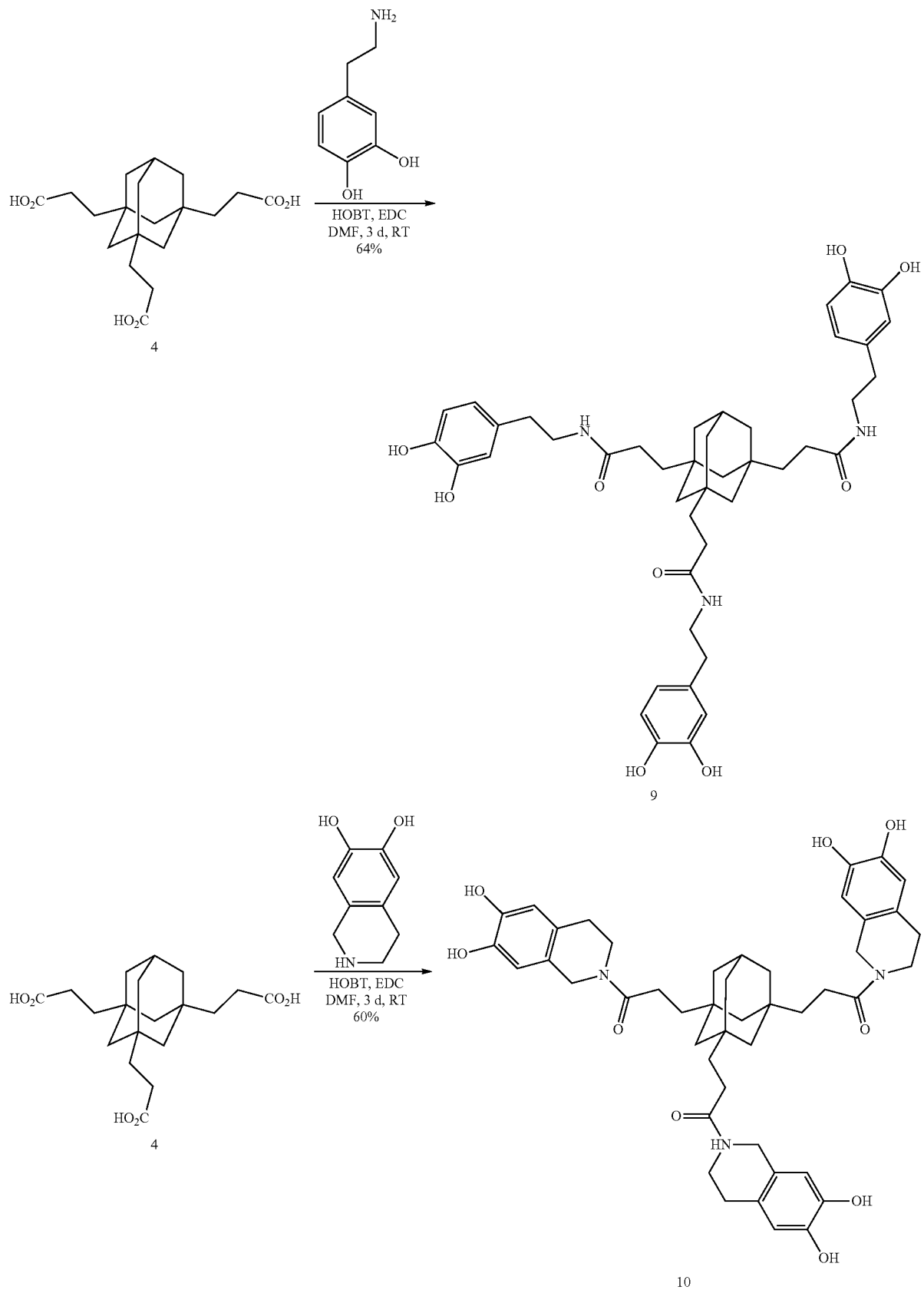

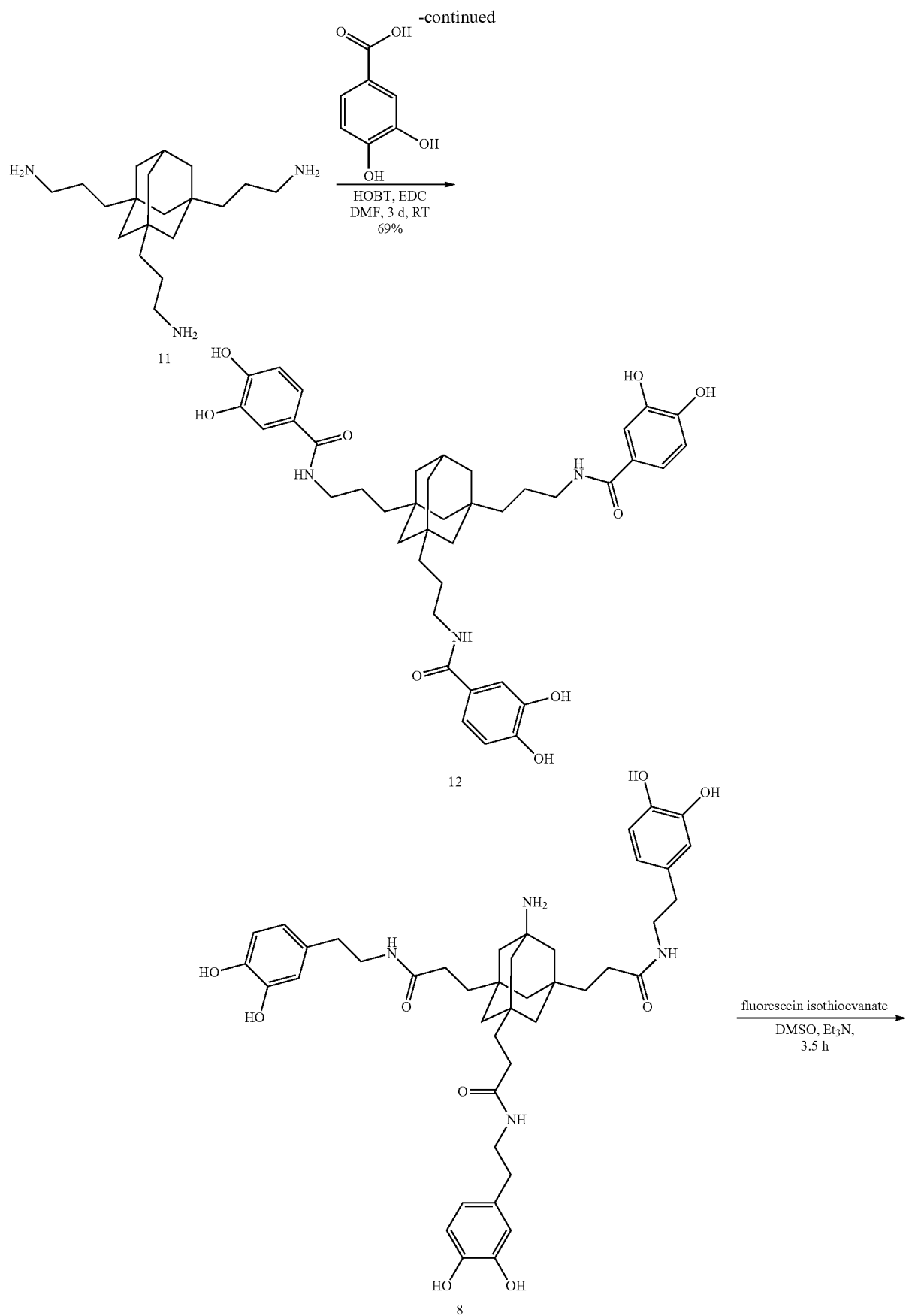

-continued

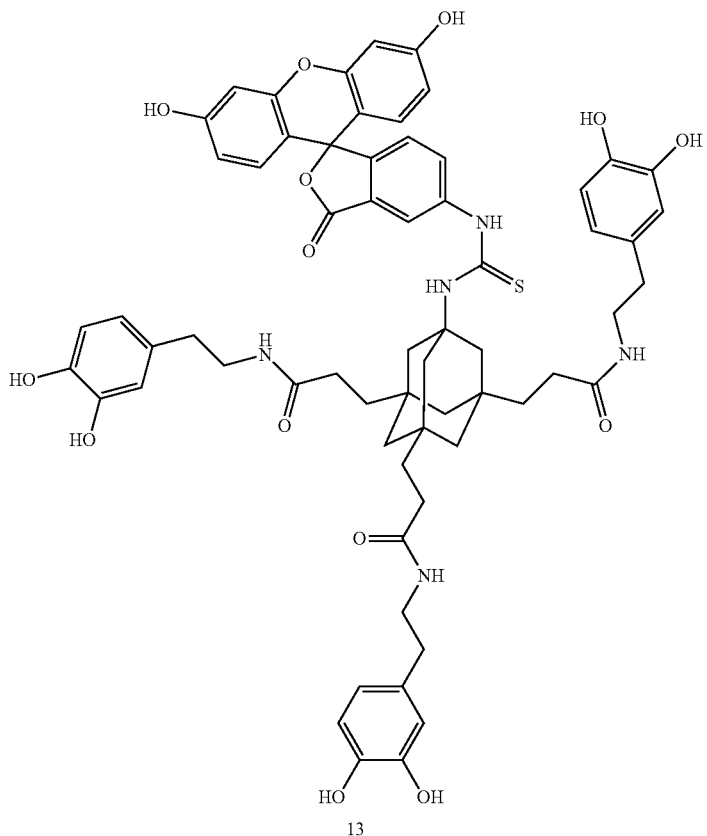 [SMILES: O=C(CCC12CC3(CCC(=O)NCCc4ccc(O)c(O)c4)CC(CCC(=O)NCCc4ccc(O)c(O)c4)(C1)CC(NC(=S)Nc1ccc4c(c1)C(=O)OC41c4ccc(O)cc4Oc4cc(O)ccc41)(C2)C3)NCCc1ccc(O)c(O)c1]

13

Practical Embodiment 1

Production of 1-(N-Cbz)-1,3,5-tris-(2-carboxyethyl)-adamantane

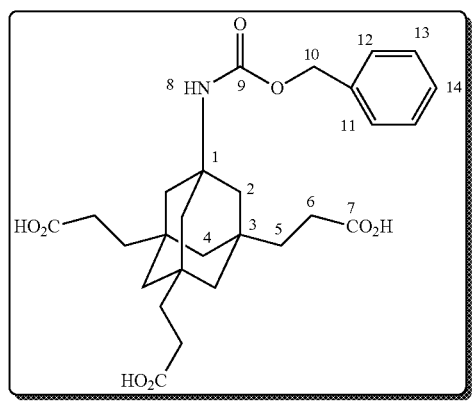

$C_{27}H_{35}NO_8$, M = 501.57 g/mol 0.3 g (4.09 mmol) $NaHCO_3$ was dissolved in 30 mL distilled water and added to a solution of 0.5 g (1.2 mmol) 1,3,5-adamantanetricarboxylic acid in 30 mL dioxane. To obtain a pH-value of approximately 9, 2M NaOH was added where necessary. 0.24 mL (1.74 mmol) CBZ-Cl was slowly added dropwise at 0° C. and stirred for 12 to 16 h (ninhydrin test). The aqueous basic phase was washed 3 times with $CH_2Cl_2$ and 3 times with ethyl acetate. It was subsequently acidified with 2M HCl to a pH-value 1, shaken out again 6 times with ethyl acetate, and the organic ethyl acetate phase was reduced using a rotary evaporator. 0.524 g (1.05 mmol) of a colourless solid 2 was able to be obtained. This corresponds to a yield of 84%.

Smp.: 221° C.; $^1$H-NMR (400 MHz, DMSO): δ [ppm]= 12.0 (br s, 3H, 7-H), 7.28-7.38 (m, 5H, aryl. —H), 7.0 (s, 1H, 8-H), 4.95 (s, 2H, 10-H), 2.13 (t, 6H, $^3J$=7.9 Hz, 6-H), 1.46 (s, 6H, 2-H), 1.37 (t, 6H, $^3J$=8.2 Hz, 5-H), 1.04 (d, 3H, $^2J$=13.2 Hz, 4a-H), 1.00 (d, 3H, $^2J$=13.2 Hz, 4b-H); $^{13}$C-NMR (400 MHz, DMSO): δ [ppm]=175.0 (C7), 154.2 (C9), 137.3 (C11), 128.4 (C13), 127.7 (C14), 127.7 (C12), 64.6 (C10), 52.0 (C1), 44.5 (C4), 44.5 (C2), 37.5 (C5), 34.3 (C3), 27.9 (C6)

Practical Embodiment 2

Production of the Compound 7 According to the Synthesis Scheme

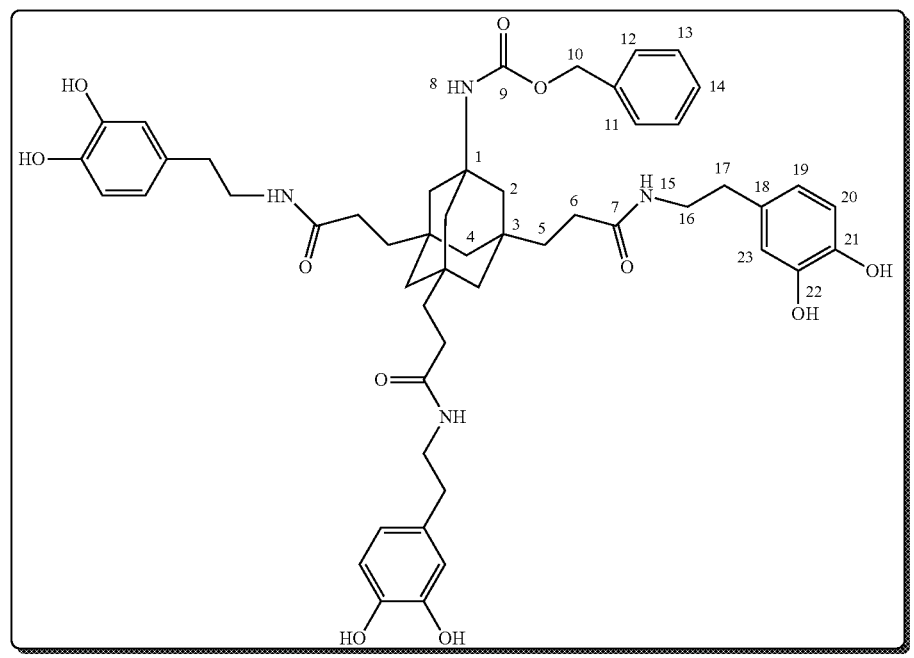

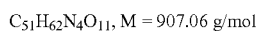

$C_{51}H_{62}N_4O_{11}$, M = 907.06 g/mol 50 mg (0.099 mmol) of the protected adamantane carboxylic acid 6 was dissolved in 30 ml abs. DMF, and 0.22 mL (01.277 mmol) DIPEA was subsequently added and stirred for 10 minutes. 63 mg (0.327 mmol) EDC*HCl (-ethyl-3-(3-dimethylaminopropyl)carbodiimide-hydrochloride) and 44 mg (0.327 mmol) HOBT (hydroxyl benzotriazole) were subsequently consecutively added and stirred for 20 min for the pre-activation. After this time, 62 mg (0.327 mmol) of the amine (dopamine hydrochloride) was added and stirred for 3 days at room temperature. Subsequently, the solvent was removed in the vacuum, taken up in 30 mL ethyl acetate and 5 mL 1M HCl and washed 3 times with the same amount of an aqueous saturated $KHSO_4$ solution. After drying over $Na_2SO_4$, the solvent was distilled off. By means of freeze drying, a beige-coloured solid was able to be obtained which was stirred 6 times respectively in 100 mL diethyl ether at 30° C. in the water bath and removed by pipette. Thus, 43 mg (0.047 mmol) of a beige-coloured solid was able to be obtained. This corresponds to a yield of 48%.

$^1$H-NMR (400 MHz, MeOH): δ [ppm]=7.17 (m, 5H, 12-14-H), 6.54 (d, 3H, $^2J$=8 Hz, 20-H), 6.5 (m, 3H, 23-H), 6.38 (d, 3H, $^2J$=8.0 Hz, 19-H), 4.84 (s, 2H, 10-H), 3.18 (m, 6H, 17-H), 2.49 (t, $^3J$=7.2 Hz 6H, 16-H), 1.97 (t, $^3J$=7.6 Hz 6H, 6-H), 1.39 (s, 6H, 2-H), 1.28 (t, $^3J$=7.6 Hz 6H, 5-H), 0.97 (d, $^2J$=12.0 Hz, 3H, 4a-H), 0.88 (d, $^2J$=12.0 Hz, 3H, 4b-H);

$^{13}$C-NMR (100 MHz, MeOH-d4): δ [ppm]=176.8 (C7), 156.7 (C9), 146.2 (C21), 144.7 (C22), 138.4 (C11), 131.9 (C18), 128.7, 128.8, 129.4 (C12-C14), 121.0 (C19), 116.9 (C23), 116.3 (C20), 66.8 (C10), 53.7 (C1), 46.3 (C4), 45.8 (C2), 42.2 (C16), 40.0 (C5), 36.0 (C3), 35.8 (C17), 31.1 (C6); MS-ESI m/z (%): (MNa$^+$)=929.6, (MH$^+$) 907.5.

Practical Embodiment 3

Production of the Compound 8 According to the Synthesis Scheme

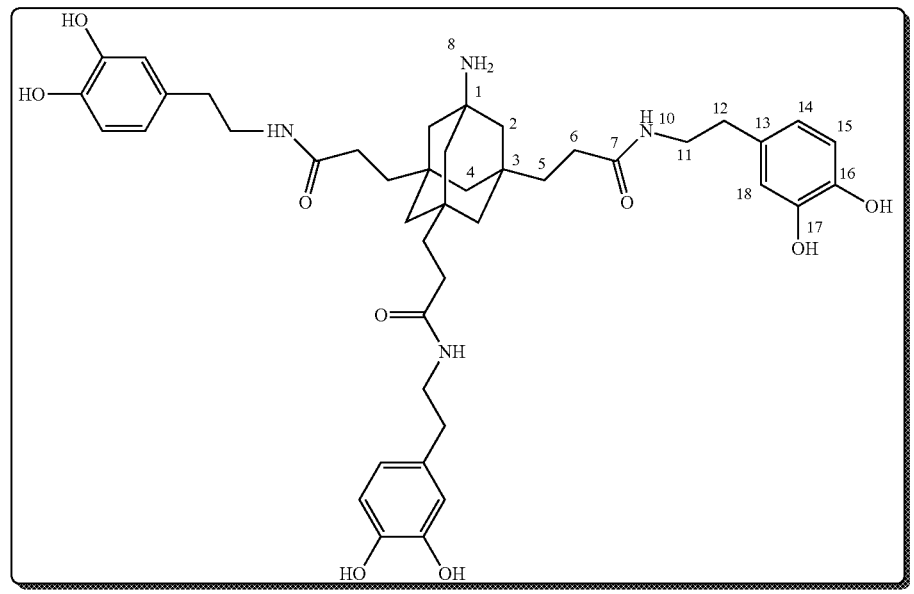

$C_{43}H_{56}N_4O_9$, M = 772.92 g/mol 43 mg (0.047 mmol) of the reaction product to be deprotected or hydrogenated from embodiment 2 was dissolved under $N_2$ atmosphere in distilled methanol, and a catalytic amount PD/c (tip of a spatula) is added. The suspension was degassed and stirred until the complete reaction is achieved under $H_2$-atmosphere for 3 days at room temperature. Subsequently, the reaction solution was filtered over a folded filter and flushed several times with distilled methanol, and the solvent was removed in the vacuum. 30 mg (0.039 mmol) of a bright yellow oil was able to be obtained. This corresponds to a yield of 82%.

$^1$H-NMR (400 MHz, MeOH): δ [ppm]=6.64 (d, 3H, $^2$J=8.0 Hz, 15-H), 6.60 (m, 3H, 18-H), 6.48 (d, 3H, $^2$J=8.0 Hz, 14-H), 2.59 (t, $^3$J=7.0 Hz 6H, 12-H), 2.08 (t, $^3$J=7.8 Hz, 6H, 11-H), 1.97 (t, $^3$J=7.6 Hz 6H, 6-H), 1.42 (m, 12H, 2-H and 5-H), 1.08 (m, 6H, 4-H);

$^{13}$C-NMR (100 MHz, MeOH-d4): δ [ppm]=176.42 (C7), 146.21 (C16), 144.79 (C17), 138.48 (C11), 132.02 (C13), 121.12 (C14), 117.05 (C18), 116.42 (C15), 54.88 (C1), 45.33 (C4), 44.95 (C2), 42.24 (C11), 49.57 (C5), 36.39 (C3), 35.80 (C12), 31.05 (C6);

MS-ESI m/z (%): ($M^+$)=772.4, ($M-H^+$)=771.5, ($2*M^+$)= 1545.3.

Practical Embodiment 4

Production of the Compound 9 According to the Synthesis Scheme 2

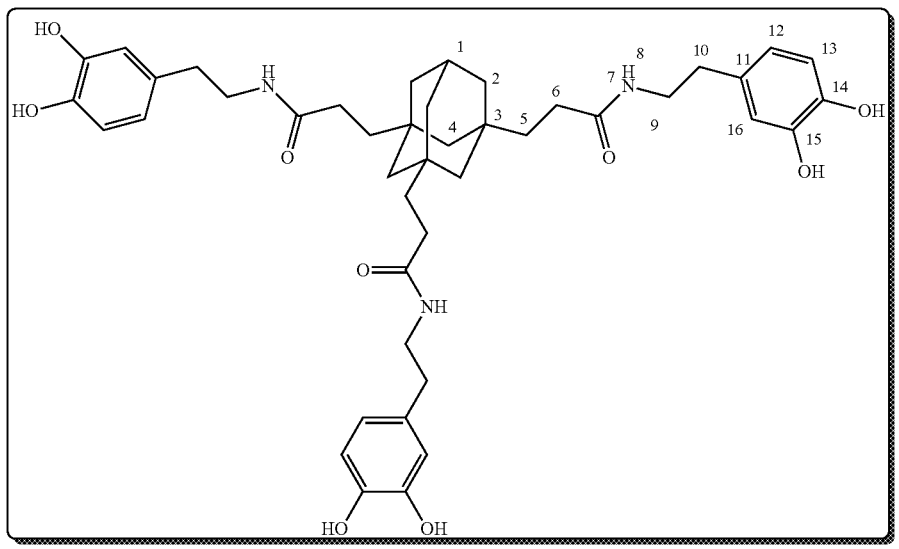

$C_{43}H_{55}N_3O_9$, M = 757.91 g/mol 500 mg (1.42 mmol) of the tricarboxylic acid 4 was dissolved in 60 mL distilled DMF and 2.54 mL distilled $Et_3N$ was added. After 5 min, 900 mg (4.69 mmol) EDC*HCL and 9.38 mL (4.69 mmol) HOAT were added at 0° C. and pre-activated for 30 min. Afterwards, 890 mg (4.69 mmol) dopamine*HCL was added and stirred for 3 days at room temperature. The solvent was removed until dry, and the crude product was dissolved in ethyl acetate, washed 3 times with saturated $KHSO_4$ solution, again reduced and stirred in diethyl ether.

687 g (0.906 mmol) of a slightly beige solid was able to be obtained. This corresponds to a yield of 64%.

$^1$H-NMR (400 MHz, MeOH): δ [ppm]=6.65 (d, 3H, $^2$J=8.0 Hz, 13-H), 6.51 (m, 3H, 16-H), 6.28 (d, 3H, $^2$J=8.0 Hz, 12-H), 3.30 (m, 6H, 10-H), 2.55 (t, 6H, $^3$J=8.0, 9-H), 2.10 (t, 6H, $^3$J=8.0 Hz, 6-H), 1.88 (s, 1H, 1-H), 1.35 (m, 12H, 2,5-H), 1.10 (m 6H, 4-H), $^{13}$C-NMR (100 MHz, MeOH): δ [ppm]=177.1 (C7), 146.2 (C14), 144.7 (C15), 131.9 (C9), 129.5 (C11), 121.0 (C16), 116.9 (C16), 116.3 (C13), 54.88 (C1), 47.3 (C4), 42.2 (C2), 41.9 (C19), 38.00 (C5), 35.8 (C3), 34.5 (C12), 31.1 (C6);

MS-ESI m/z (%)=757.3 [M]$^+$ (38), 758.3 [MH]$^+$ (45), 780.3 [MNa]$^+$ (32)

Practical Embodiment 5

Production of the Compound 10 According to the Synthesis Scheme 2

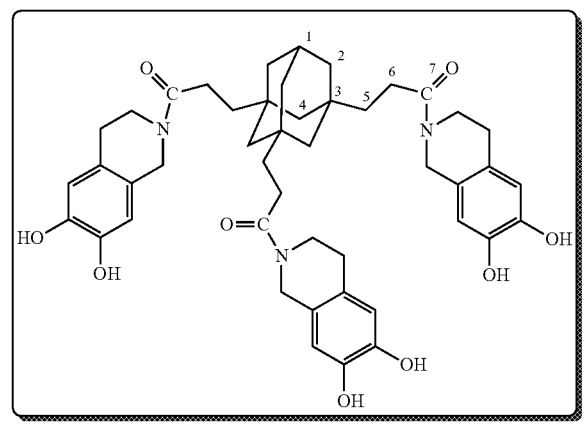

$C_{46}H_{55}N_3O_9$, M = 793.94 g/mol 100 mg (0.28 mmol) of the tricarboxylic acid 4 was dissolved in 30 mL distilled DMF, and 0.51 mL distilled $Et_3N$ was added. After 5 min, 180 mg (0.93 mmol) EDC*HCL and 126 mg (4.69 mmol) HOBT were added and pre-activated for 5 min. Afterwards, 231 mg (937 mmol) 1,2,3,4-tetrahydro-6,7-isoquinolinediorhydrobromide was added and stirred for 5 days at room temperature. The solvent was removed until dry, and the crude product was dissolved in ethyl acetate, washed 3 times with saturated $KHSO_4$ solution, dried over $Na_2SO_4$, again reduced and stirred in diethyl ether. After filtration and removal of the solvent, 133 mg of the target compound 10 (60%) remains.

MS-ESI m/z (%)=794.4 [MH$^+$] (75%)

Practical Embodiment 6

Production of the Compound 12 According to the Synthesis Scheme 2

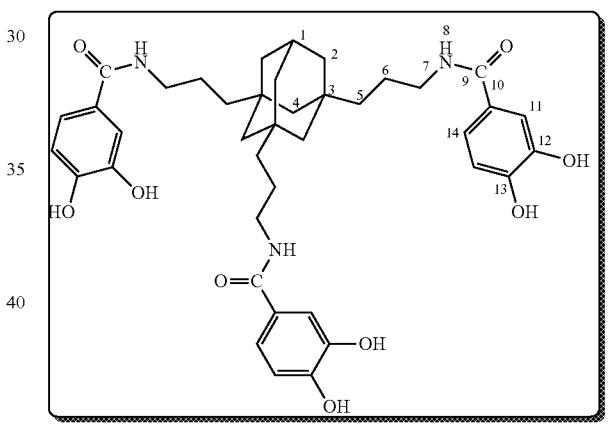

$C_{40}H_{49}N_3O_9$, M = 715.83 g/mol 200 mg (0.48 mmol) of the triamine 11 was dissolved in 30 mL distilled DMF, and 0.85 mL distilled $Et_3N$ was added. After 5 min, 303 mg (1.58 mmol) EDC*HCL and 214 mg (1.58 mmol) HOBT were added and pre-activated for 15 min. Afterwards, 251 mg (1.58 mmol) 3,4-dihydroxybenzoic acid was added and stirred for 5 days at room temperature. The solvent was removed until dry, and the crude product was dissolved in ethyl acetate, washed 3 times with saturated $KHSO_4$ solution, dried over $Na_2SO_4$, again reduced and stirred in diethyl ether. After filtration and removal of the solvent, 237 mg of the target compound 10 (69%) remains.

MS-ESI m/z (%)=716.4 [MH$^+$] (100%)

Practical Embodiment 7

Production of the Compound 13 According to the Synthesis Scheme 2

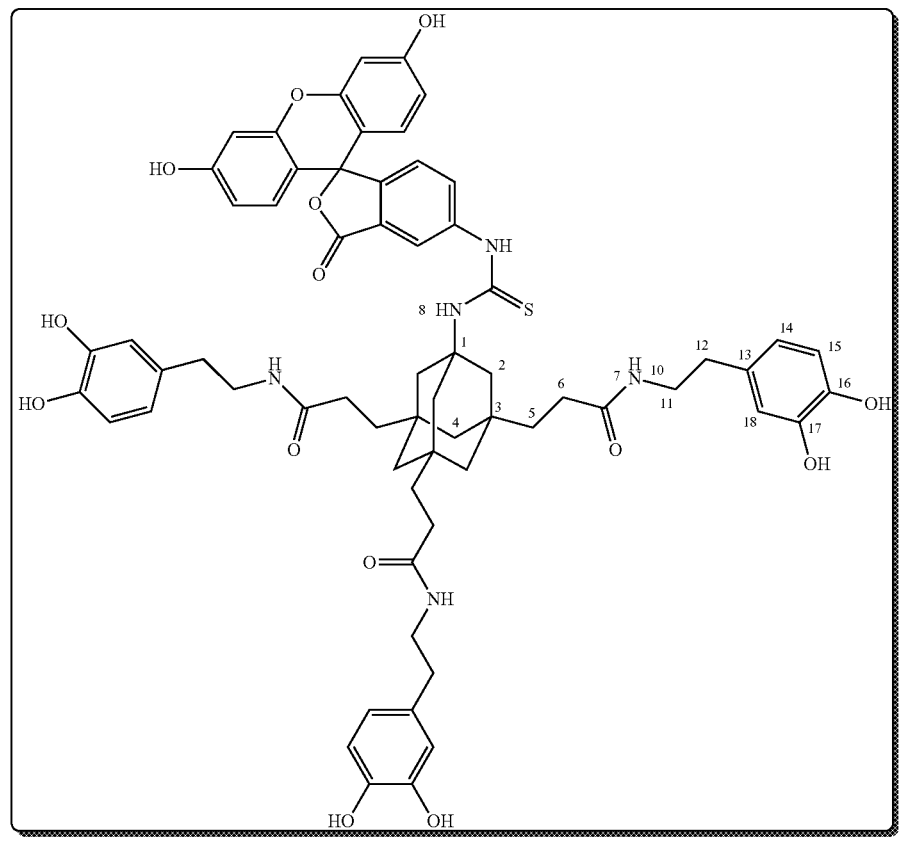

$C_{64}H_{67}N_5O_{14}S$, M = 1161.44 g/mol 21 mg (0.03 mmol) of the compound 8 was dissolved in 15 mL distilled DMSO and 0.15 mL distilled $Et_3N$ and 10 mg (0.03 mmol) fluoroscein inisothiocyanate were added and stirred at room temperature for 3.5 hours. The solvent was removed until dry, and the crude product was used without further purification for the surface functionalisation.

Practical Embodiment 8

Surface Modification

For the surface modification, $TiO_2$ surfaces on Si wafers are used. For that purpose, a solution from $TiCl_4$, water and ethanol is produced, and the Si wafers are dipped in and extracted at a speed of 1 mm/sec. In the oven, the surfaces are "burnt" into their final form. For that purpose, the Si wafers are heated to 80° C. over 6 h, then for 6 h to 300° C., and then with a heating rate of 10° C./min to 550° C.

The compounds (5 mg each) according to the present invention are dissolved in 5 mL MeOH and 15 mL pure HPLC water.

For the dipcoating method, 100 mL buffer stock solution (0.1 mol/Mops) is produced from 3.5 g NaCl, 10.45 g $K_2SO_4$ and 2.31 g Mops (=3-morpholinopropane-1-sulfonic acid). For that purpose, also pure HPLC water is used.

5 mL of the solvent of each compound according to the present invention and 10 mL buffer stock solution are mixed and the $TiO_2$ surfaces are coated by means of dip-coating for 13 h.

After this reaction time the surfaces are purified with distilled MeOH and distilled water, dried by means of air pressure and measured by means of contact angle measurement and SIMS-T of.

Practical Embodiment 9
Contact Angle Measurement
The following substances have been measured:
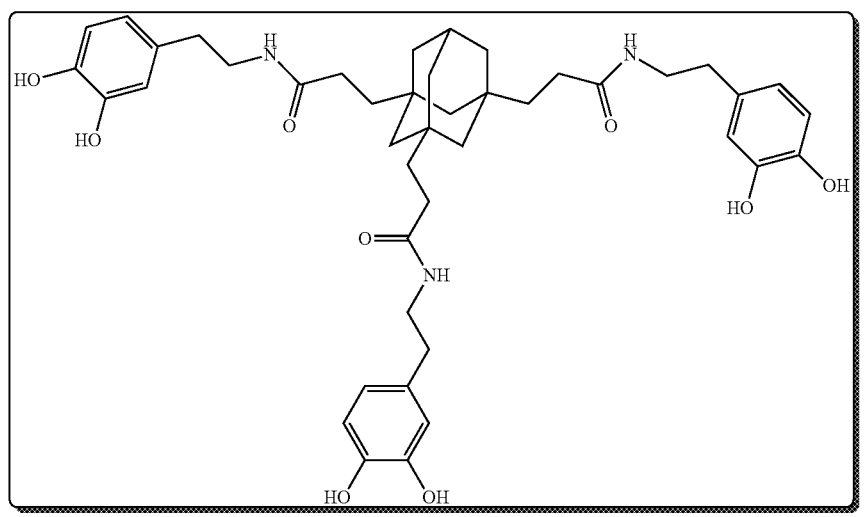
3
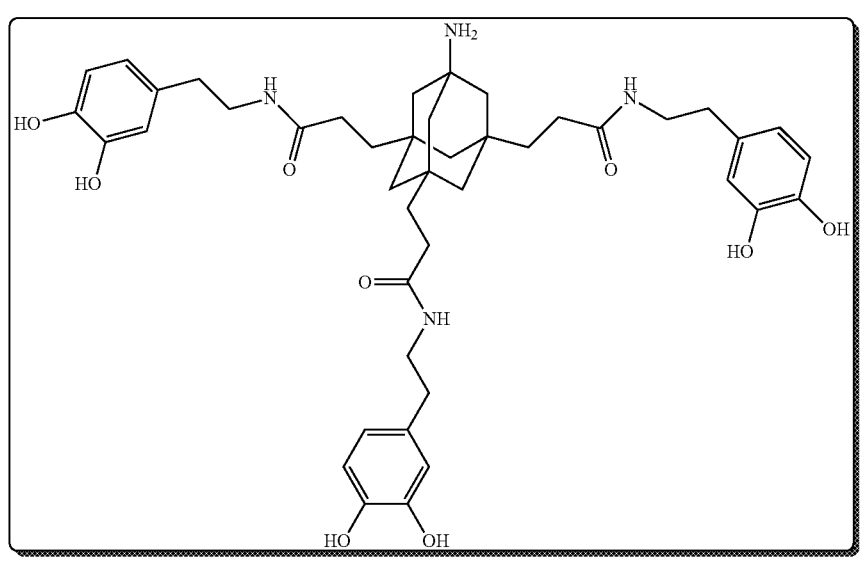
4

-continued

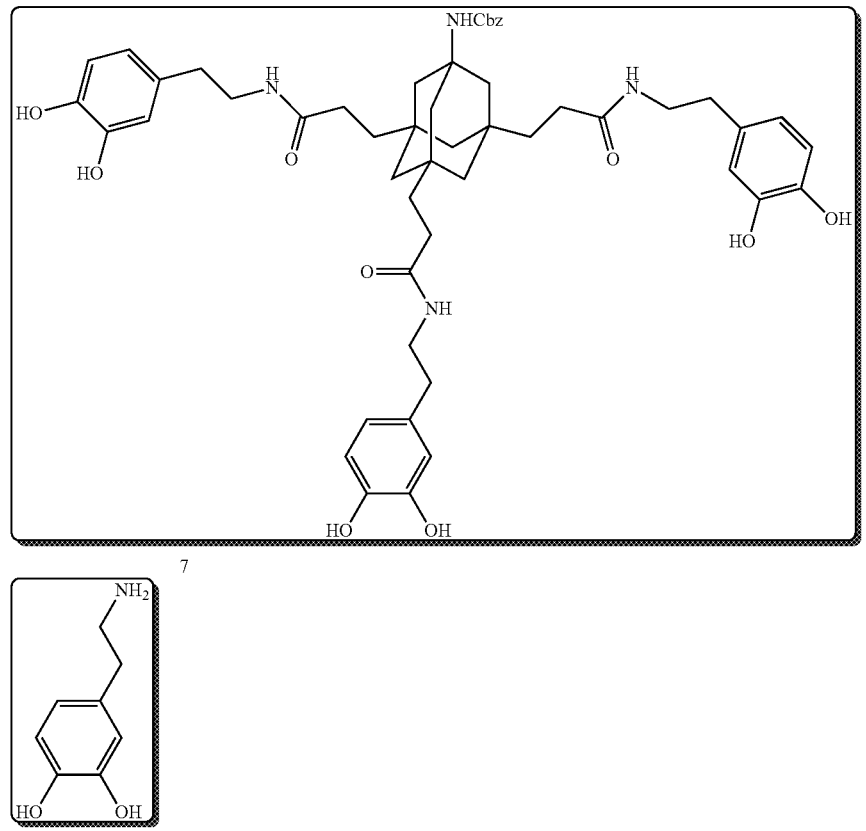
5

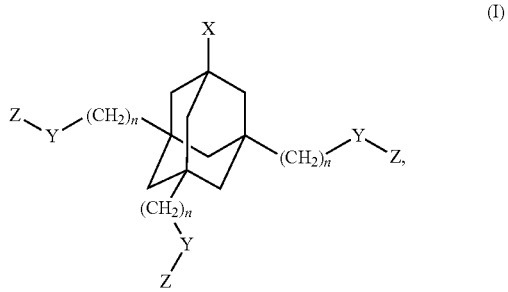
7

Before each measurement, the $TiO_2$ surfaces to be measured are purified from dust and drops of water by means of air pressure.

A contact angle measurement device (Kruss Dropshape Analyser, DAS 10-MK 2) was used for the measurement, wherein a constant temperature of 23° C. was obtained in the measurement chamber. A needle which produced a drop of water (HPLC grade water) of 4 µl was driven slowly to the surface in order to displace the drop onto the surface.

From this point onwards, a camera took a sequence of 1,000 photos which were manually analysed at the end with the help of specific computer software (Krüss, DSA=Drop Shape Analyse) which uses the Young-Laplace method (Sessel Drop Fitting).

Each $TiO_2$ surface was measured 3 to 4 times, and the mean value was determined from the results.

A pure, purified $TiO_2$ sheet without coating (second column in table 1) and the $TiO_2$ sheet coated with Mops buffer (column 3 in table 1) were measured as controls, respectively. Column 4 shows the results of the contact angle measurements of $TiO_2$ sheets, which had been coated with 3 to 7 ("molecules") substances dissolved in Mops buffer.

TABLE 1

Results of the contact angle measurement

| Substance no. | $TiO_2$ Contact angle (°) | $TiO_2$ + Mops Contact angle (°) | $TiO_2$ + Mops + molecules Contact angle (°) |
|---|---|---|---|
| 3 | 28.0 | 5.0 | 38.5 |
| 4 | 29.1 | 5.0 | 11.7 |

TABLE 1-continued

Results of the contact angle measurement

| Substance no. | $TiO_2$ Contact angle (°) | $TiO_2$ + Mops Contact angle (°) | $TiO_2$ + Mops + molecules Contact angle (°) |
|---|---|---|---|
| 5 | 24.7 | 8.2 | 22.9 |
| 7 | 30.9 | 7.6 | 10.7 |

The invention claimed is:

1. A compound according to formula (I)

$$(I)$$

wherein
n is an integer between 0 and 10,
Y is a bond, —$CH_2$—, —CH=CH—, —C≡C—, —O—, —S—, —S—S—, —NH—, —O—NH—, —NH—O—, —HC=N—O—, —O—N=CH—, —$NR^1$—, -aryl-, -heteroaryl-, —(C=O)—, —O—

—(C=O)—, —(C=O)—O—, —NH—(C=O)—, —(C=O)—NH—, —NR¹—(C=O)—, —(C=O)—NR¹—, —NH—(C=O)—NH—, or —NH—(C=S)—NH—,

R¹ is a linear alkyl group with 1 to 10 C atoms or for a branched or cyclic alkyl group with 3 to 10 C atoms, Z is selected from

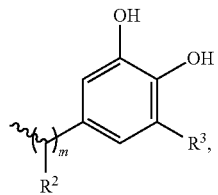

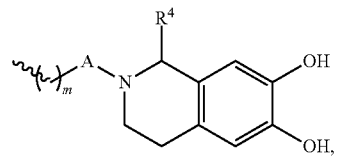

m is an integer between 0 and 10,
R² is —H, —OH or —COOH,
R³ is —H or —OH,
A is a bond or —(C=O)—,
R4 is —H or

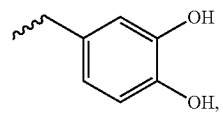

X is —(CH₂)$_p$—R⁵; a branched alkyl, alkenyl or alkynyl group with 3 to 10 C atoms; a cyclic alkyl, alkenyl or alkynyl group with 3 to 10 C atoms; or an aryl or heteroaryl group, p is an integer between 0 and 10

R⁵ is —H, —NH₂, —NO₂, —OH, —SH, —O—NH₂, —NH—NH₂, —N=C=S, —NC=O, —CH=CH₂, —C≡CH, —COOH, —(C=O)H, or —(C=O)R⁶, wherein the hydroxy, thio, amino or C=O groups are optionally suitable to be protected by a protective group, —N₃, —OR⁶, —COOR⁶, —NHR⁶, —NR⁶R⁷, —CO—NHR⁶, —CONR⁶R⁷, —NH—CO—R⁶, or 4-(2,5-dioxopyrrol-1-yl), and R⁶ and R⁷ each, independently, is a linear alkyl group with 1 to 10 C atoms, a linear alkenyl or alkynyl group with 2 to 10 C atoms, or a branched alkyl, alkenyl or alkynyl group with 3 to 10 C atoms, wherein, if X is a branched alkyl, alkenyl or alkynyl group, a cyclic alkyl or alkenyl group, an aryl or heteroaryl group, then one C atom of this group X is optionally substituted with R⁵.

2. The compound according to claim 1, wherein Y is a bond, —CH₂—, —NH—(C=O)—, —(C=O)—NH—, or —NR¹.

3. The compound according to claim 1, wherein n is an integer between 0 and 3.

4. The compound according to claim 1, m is an integer between 0 and 3.

5. The compound according to claim 1, wherein Z is

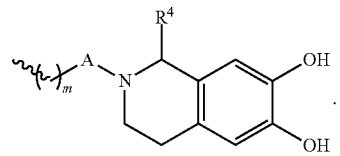

6. The compound according to claim 1, wherein the group YZ is selected from

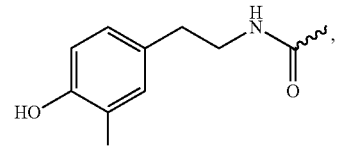

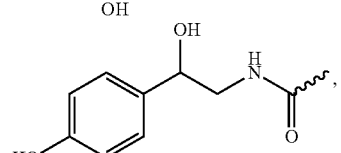

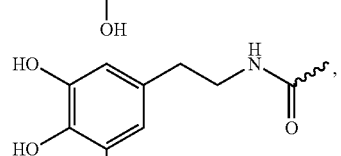

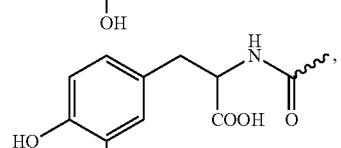

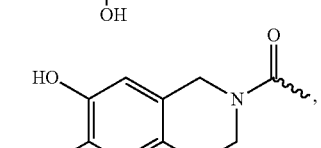

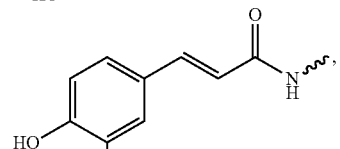

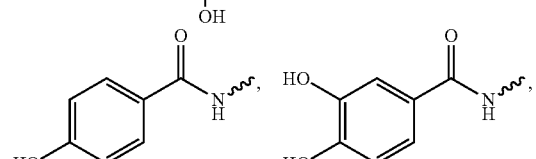

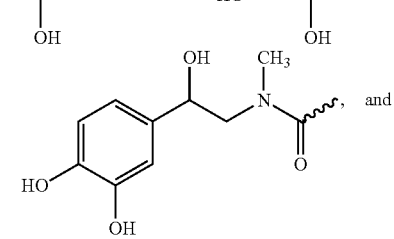

-continued

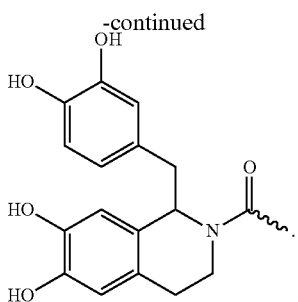

7. The compound according to claim 1, wherein X is —(CH$_2$)$_p$—R$^5$, and p is an integer between 0 and 3.

8. The compound according to claim 1, wherein
X is —(CH$_2$)$_p$—R$^5$,
R$^5$ is —H, —OH, —NH$_2$, —NO$_2$, —NH—NH$_2$, —NHR$^6$, —NR$^6$R$^7$, —O—NH$_2$, —NH—(C=O)—C≡CH, —C≡CH, —N=C=S, —N=C=O, —COOH, —(C=O)H, or —(C=O)R$^6$, and
p is an integer between 0 and 3.

9. A method for the production of a compound according claim 1, the method comprising:
reacting a compound X-Ad[(CH$_2$)$_n$—Y']$_3$ with a reagent Y"Z to produce X-Ad[(CH$_2$)$_n$—YZ]$_3$ as a reaction product, and
purifying the reaction product,
wherein Ad is the adamantyl skeleton, Y' and Y" and precursors of Y.

10. The method according to claim 9, wherein X is a hydrogen atom.

11. The method according to claim 9, wherein
X is —(CH$_2$)p—R$^5$,
R$^5$ is —OH, —NH$_2$, —NO$_2$, —NH—NH$_2$, —NHR$^6$, —NR$^6$R$^7$, —O—NH$_2$, —NH—(C=O)—C≡CH, —C≡CH, —N=C=S, —N=C=O, —COOH, —(C=O)H, or —(C=O)R$^6$, and
p is an integer between 0 and 3.

12. The method according to claim 11, wherein R$^5$ is protected by a protective group (Pg) prior to reacting the compound with the reagent Y"Z, so that the compound Pg-X-Ad[(CH$_2$)$_n$—Y']3 is reacted with the reagent Y"Z to produce a corresponding compound Pg-X-Ad[(CH$_2$)$_n$—YZ]3.

* * * * *

UNITED STATES PATENT AND TRADEMARK OFFICE
CERTIFICATE OF CORRECTION

PATENT NO. : 8,785,641 B2
APPLICATION NO. : 13/821319
DATED : July 22, 2014
INVENTOR(S) : Wolfgang Maison et al.

Page 1 of 1

It is certified that error appears in the above-identified patent and that said Letters Patent is hereby corrected as shown below:

On the Title Page:

Item (73) Assignee "Justus-Liebig-Universitat Giessen" should be

-- Justus-Liebig-Universitaet Giessen --.

Signed and Sealed this
Seventh Day of October, 2014

Michelle K. Lee
*Deputy Director of the United States Patent and Trademark Office*